(12) United States Patent
Müller et al.

(10) Patent No.: US 8,801,671 B2
(45) Date of Patent: Aug. 12, 2014

(54) INFUSION SET COMPRISING A DATA DISPLAY AND METHOD THEREOF

(75) Inventors: Marcel Müller, St. Gallen (CH); Franco Moia, Frenkendorf (CH)

(73) Assignee: Roche Diagnostics International AG, Rotkreuz (CH)

( * ) Notice: Subject to any disclaimer, the term of this patent is extended or adjusted under 35 U.S.C. 154(b) by 539 days.

(21) Appl. No.: 12/878,147

(22) Filed: Sep. 9, 2010

(65) Prior Publication Data

US 2011/0066118 A1    Mar. 17, 2011

(30) Foreign Application Priority Data

Sep. 10, 2009 (EP) .................................... 09169966

(51) Int. Cl.
*A61M 3/00* (2006.01)
(52) U.S. Cl.
USPC .................. 604/189; 604/164.04; 604/174
(58) Field of Classification Search
USPC ............................................. 604/174, 189
See application file for complete search history.

(56) References Cited

U.S. PATENT DOCUMENTS 7,817,498 B1 * 10/2010 Hinckley ........................ 368/10

FOREIGN PATENT DOCUMENTS

| WO | 2004114256 A2 | 12/2004 |
| WO | 2006045525 A1 | 5/2006 |
| WO | 2006124936 A2 | 11/2006 |
| WO | 2007028200 A1 | 3/2007 |
| WO | 2007134066 A2 | 11/2007 |
| WO | 2008091164 A1 | 7/2008 |

OTHER PUBLICATIONS

International Search Report, Feb. 16, 2010 for International Application No. EP 09169966.0, pp. 1-6.

* cited by examiner

*Primary Examiner* — Emily Schmidt
(74) *Attorney, Agent, or Firm* — Dinsmore & Shohl, LLP (57) ABSTRACT

Included are embodiments of an infusion set for administering a liquid. One embodiment includes an infusion head to be placed on the tissue of a patient, a coupler for connecting the infusion head to an administering device, and a cannula that is configured for connection to the infusion head. Some embodiments include a display device for displaying an application period of at least a portion of the liquid administered using the infusion set.

7 Claims, 6 Drawing Sheets

INFUSION SET COMPRISING A DATA DISPLAY AND METHOD THEREOF

CROSS REFERENCE TO RELATED APPLICATION

This application claims the priority to European Application Number EP09169966, filed Sep. 10, 2009, which is hereby incorporated by reference in its entirety.

TECHNICAL FIELD

This disclosure relates generally to systems and method for administering a liquid to a patient, and in particular to an infusion set comprising a data display and method thereof.

BACKGROUND

In elderly people's homes and nursing homes it is often difficult to ensure that disposable materials are changed within a time scale recommended by the manufacturer. The application period and/or expiry date of the materials are often only provided on the outside of the packaging, while the disposable material itself is not provided with these dates. Similarly, with many current disposable materials, the color of the packaging can change or a sound can be produced by an audio device, upon reaching the expiry date. This may be part of the packaging, such that a certain period after the packaging seal has been broken, the change can and/or sound can be implemented. Another area of application is the use of infusion sets for insulin pump therapy, in which the infusion sets are replaced by the diabetic themselves or a relative. Experience has shown that, even if these persons are not especially handicapped and despite the fact that they are specifically trained, they often forget to replace the disposable materials, resulting in reduced insulin absorption in the tissue and complications such as for example inflammation.

Other current implementations include noting the relevant data on a separate protocol sheet, using an infusion set clock (which is a device similar to a parking disc), and disabling the infusion set electronically if the infusion set includes an integral data memory.

SUMMARY

Included are embodiments of an infusion set for administering a liquid. One embodiment of a system includes an infusion head to be placed on the tissue of a patient, a coupler for connecting the infusion head to an administering device, and a cannula that is configured for connection to the infusion head. Some embodiments include a display device for displaying an application period of at least a portion of the liquid administered using the infusion set.

BRIEF DESCRIPTION OF THE DRAWINGS

The contents of this disclosure will now be illustrated on the basis of different embodiments. All the features described in connection with the figures and/or shown in the figures form part of this disclosure.

DETAILED DESCRIPTION

The embodiments of this disclosure may help to reduce the risk of missing expiry date and/or application period deadlines for disposable materials such as, e.g., an infusion set without a significant rise in cost. Embodiments of an infusion set for administering a liquid, as well as methods for recording an expiry date are disclosed herein.

One embodiment of this disclosure relates to an infusion set for administering a liquid, preferably a medical liquid such as liquid insulin, that includes an infusion head to be placed on the tissue of a patient. Some embodiments include a coupler for connecting the infusion head to an administering device and a cannula, which is or can be connected to the infusion head and optionally an apparatus for placing the infusion head on the tissue. In such embodiments, the infusion set may include a setting device for displaying an expiry date and/or an application period of the infusion set or a part of the infusion set or the liquid administered using the infusion set.

Additionally, in some embodiments, the infusion set or at least parts of the infusion set are disposable. The infusion head, the coupler and the cannula are normally only used once, while the device for displaying the expiry date and/or application period and the apparatus for placing the infusion head can be reused. Thus, the infusion set can be provided as an integrated assembly in such a way that disassembling the infusion set is tantamount to dismantling the infusion set, after which it can no longer be used.

In one embodiment, the display device includes a special transfer region that can be provided in such a way as to seal the transferred image such that it cannot be smeared or wiped off. Additionally, the transfer region can include a material that allows the relevant data to be embossed. The image can be transferred onto the infusion set by a stamping unit, embossing unit, or any other suitable device. If a stamping unit is used, it can be a commercially available mechanical or electronic stamping unit with or without a text plate.

In another embodiment, the display device is supplied in the form of a sticker that is preferably already applied to the infusion set or part of the infusion set or which could also be applied by the medical staff when needed. The sticker preferably exhibits a design that allows the staff to mark the day and/or date on which the infusion set is applied to the patient and/or the date of the beginning and/or the end of an application period. The sticker can, for example, be circular in shape and can include a partition that corresponds to the maximum period allowed or a partition that allows the day of the week on which the infusion set is applied to the patient to be marked. Many other partitions are possible, depending on the dates and/or periods which need to be monitored.

In another embodiment, the display device is provided as a mechanical display which is preferably connected to the infusion set or to a part of the infusion set. This mechanical display can, for example, include at least two releasable parts, which may be embodied as ring elements or discs, which can be rotated relative to each other. One of the releasable parts may include a set of numbers and the releasable part includes, for example, an arrow in order to mark the beginning and/or ending of an application. If a period is to be marked, two arrows are utilized, which can be achieved by using three rings or three discs or by incorporating two separate arrows that can be moved relative to a base plate that displays the countermarks. The mechanical display is preferably reusable. In order to ensure that the set date or period cannot be randomly changed, it may be advantageous if the different parts can be secured in their set position and only disengaged after the display has been removed from the infusion set. Instead of two ring elements or discs, it is also possible to use two or more parallel bars which can be moved linearly with respect to each other in order to set a date or the beginning and/or end of a period.

Instead of a mechanical display, an electronic display can be used with the infusion set. The electronic display is likewise preferably a reusable display which can be used repeatedly. In order to ensure that the data on the electronic display are neither deleted by accident nor manipulated, it may be advantageous if the display can be activated either by hand or remote control and the necessary data can be set within a particular period of time. Once the time period has expired, the display can only be reset if it is disconnected from the infusion set, where the display and the infusion set can preferably only be disconnected if the infusion set has been removed from the patient. The electronic infusion set may be initiated automatically on its activation day and/or time, for example via a wireless connection between the display and a reference clock.

One embodiment of an infusion set disclosed herein can include an apparatus for placing the infusion head on the tissue of a patient. If such an apparatus is used, it is within the scope of this disclosure for the apparatus to include a device for transferring the relevant information onto the infusion head. This transferring device can be provided in the form of a stamping unit that transfers the date onto the surface of the infusion head. As described above, some embodiments may be configured such that the region in which the stamping unit is to be applied is provided in such a way as to prevent the transferred data from being smeared or wiped off and/or in such a way as to allow the data to be embossed.

The integrated stamping unit can preferably be mechanically manipulated in order to show the correct date and/or period. Similarly, the upper side of the infusion head can already be provided with a date and/or period scale, where the stamping unit in the apparatus then merely includes one or more arrows that indicate the start or end of a period. If only one arrow is used, this arrow can be in a fixed position in the apparatus, for example pointing in a direction which is marked on the outside of the apparatus. In this case, the staff personnel may have to insert the infusion head into the apparatus in such a way that the arrow will be printed onto the part of the infusion head representing the correct day and/or date. Printing includes the use of stick-on arrows which are transferred onto the infusion head using the apparatus.

If more than one arrow is utilized, for example in order to mark the beginning and the end of a period, the arrows can be rotated in their position by hand or with the aid of a simple mechanism. Periods can also be marked by partially covering the stamping unit so that only the relevant number of days is shown.

In some embodiments, reusable indication units may be manually positioned on the infusion head prior to or after positioning the infusion head on the tissue of the patient. The apparatus can also be used to deliver these indication units together with the infusion head. Examples of reusable displays have been described above, but another example of a reusable display that can be applied to the infusion head with the aid of the apparatus is for example that of an electronic indication unit, preferably including: one or more illuminants, a liquid crystal display (LCD) or a passive electronic indicator, such as light emitting diodes (LED) and/or organic light emitting diodes (OLED). Such an embodiment may also include a power supply, such as a rechargeable battery and an electronic timer or the like. The electronic indication unit can be activated the moment it is fixed to the infusion head. The electronic indication unit may be configured to carry the information of a given expiry date and/or end of an application period. It can be activated by the transfer and go out once the end of the period has been reached, or can be activated only once the end of the period has been reached. It is also possible for the indication unit to initially shine in a first color (for example green) when activated and to change color once the end of the pre-set period has been reached. If the indication unit comprises more than one illuminant, the illuminants can shine at different times in different colors, for example in the manner of traffic lights. The illuminants can initially all shine in the same color and, depending on the elapsed time, change color one by one, illuminate one after the other or go out subject to the elapsed time.

Additionally, the indication unit itself contains the energy necessary for illumining, for example in the form of a rechargeable battery. This energy will degenerate with time. To allow the display to be used repeatedly, it is preferable for the indication unit to be rechargeable, either at a separate station or within the apparatus which is then preferably provided with a rechargeable energy storage. The apparatus can then be recharged at a charging station. Additionally or alternatively, the apparatus can include a photovoltaic element that at least assists in charging. If the apparatus itself is the charging station for the indication unit, then it preferably comprises a control light which indicates the energy storage level and whether the apparatus needs to be recharged at the charging station. For reasons of energy consumption, the apparatus can be designed such that it is possible to activate the electronic indicator only "on demand," for example via an on-button, a Reed relay, or the like.

In another embodiment, the apparatus can include a wireless connection such as a BLUETOOTH facility, which connects the apparatus, for example, to an electronic device such as a laptop, a smart phone, a diabetes manager, an insulin pump, a stationary computer, or the internet. The time at which the infusion set is applied to the patient can then be automatically transferred to the computer, which can monitor the expiry date and/or the end of the application period and generate a signal to inform the staff or the user that the expiry date and/or the end of the application period has been reached.

The apparatus can additionally be connected to a stock or warehouse in order to constantly monitor the amount of infusion sets in stock and to cause a replacement order to be automatically filed when the amount of infusion sets in stock falls below a given number.

Figure 1:
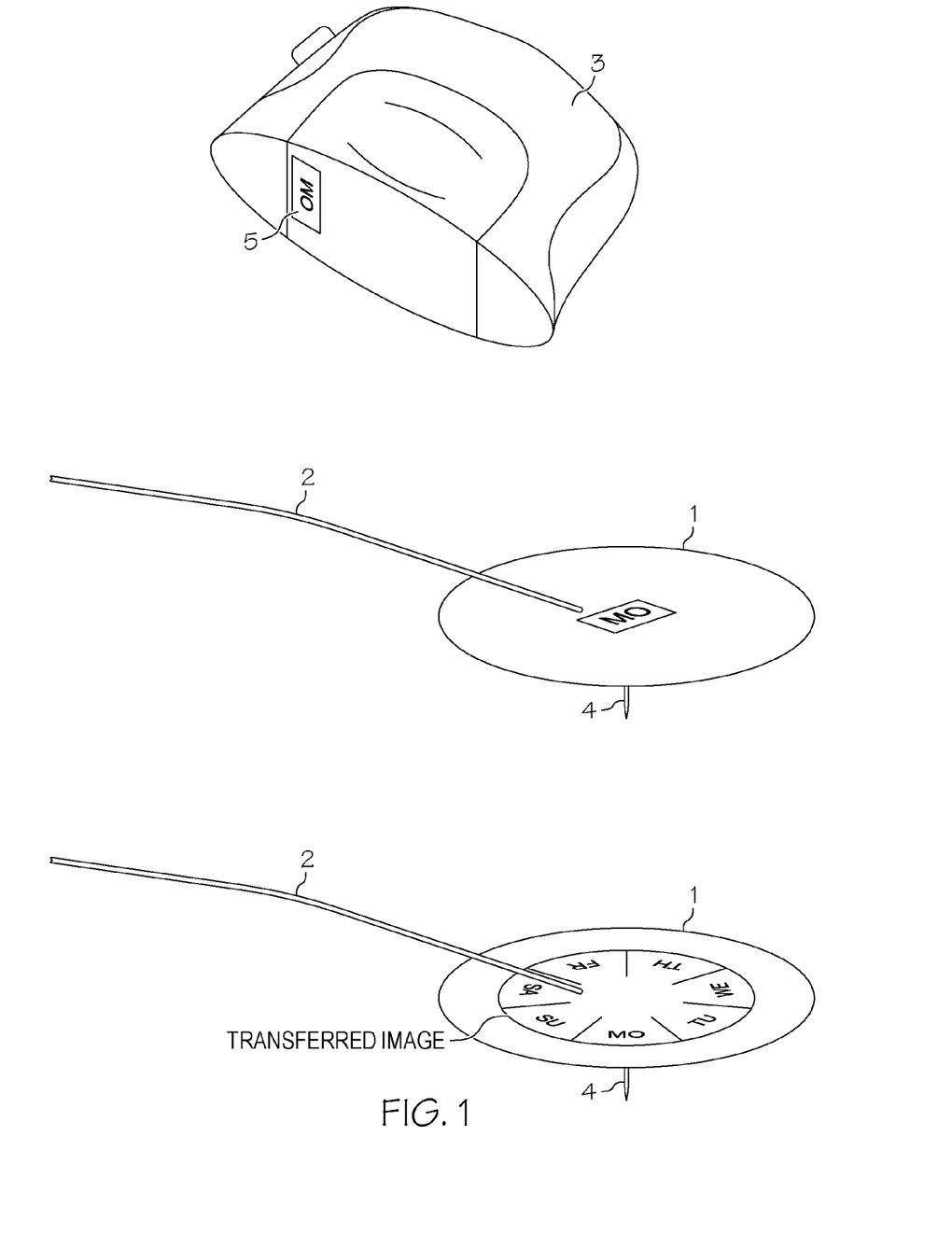
FIG. 1 depicts an apparatus that includes an integrated date stamping unit and a stamped infusion head including a display device as a transferred image, in accordance with various embodiments.

Referring now to the drawings, FIG. 1 shows an infusion head 1 including a cannula 4 and a coupler 2 of an infusion set (which may be embodied as a tube), and an apparatus 3 that can be used to place the infusion head 1 on the tissue of a patient. The apparatus 3 includes an integrated stamping unit 5 that transfers an image, for example a series of numbers representing the expiry date of the infusion set, onto the infusion head 1. In order to guarantee that the transferred image is easily legible and to protect the image against smearing, the upper side of the infusion head 1 or at least parts of it can be provided with a special layer that fixes the transferred image on the upper side of the infusion head 1. The date on the apparatus 3 can preferably be set by a mechanism incorporated in the apparatus 3.

Figure 2:
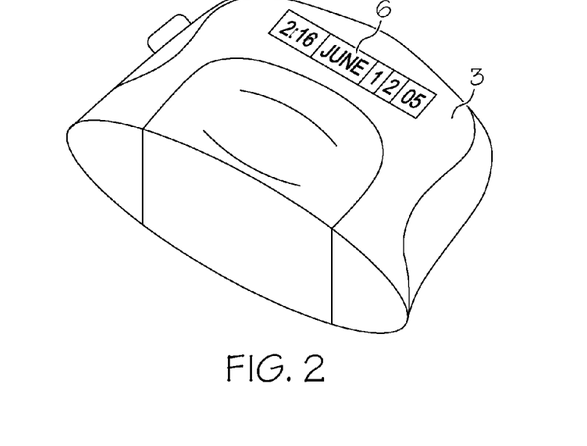
FIG. 2 depicts an apparatus that includes an integrated mechanical date display, in accordance with the various embodiments.

In order to enable the user or the staff to set the date, the apparatus 3 can include a mechanical date display 6 as shown in FIG. 2. The date shown in the mechanical date display 6 is transferred to the upper side of the infusion head 1, when the infusion head 1 is placed in the apparatus 3 or when the infusion head 1 is applied to the tissue of the patient. The ink used to transfer the image onto the infusion head 1 can be stored in a reservoir inside the apparatus 3. Similarly, the apparatus 3 can be pressed onto an ink pad prior to connecting the infusion head 1 to the apparatus 3. If an application period is to be represented by the image, it is possible to set the beginning and/or the end of said period with the aid of the apparatus 3 and to generate an image as shown on the infusion head 1 in FIG. 2.

Figure 3:
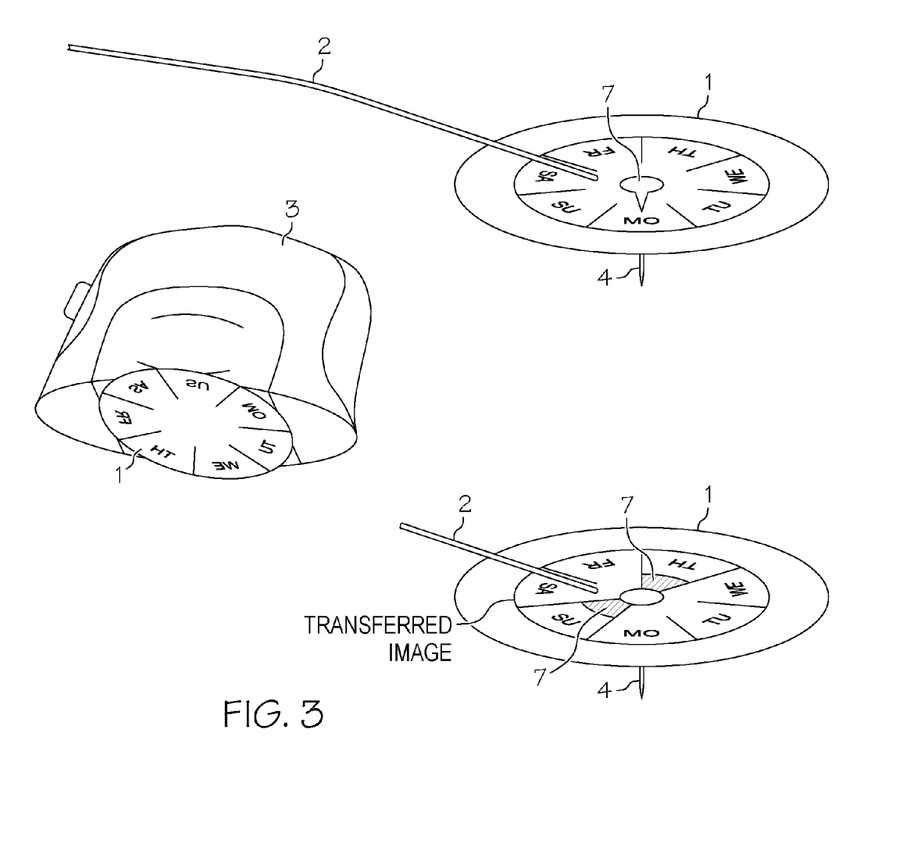
FIG. 3 depicts an apparatus that includes an infusion head with a including a display device as a date scale printed on it before it is applied, includes a first infusion head with an arrow printed on it which for example identifies the expiry date, and additionally includes a second infusion head with two arrows printed on it which identify an application period, in accordance with the various embodiments.

FIG. 3 shows the infusion head 1 after it has been placed in the apparatus 3, wherein the infusion head 1 has been pre-printed with a time scale not only on the upper side but also on the plaster side in order to allow the user to place the infusion head in a desired position in the apparatus. The apparatus 3 can then be used to mark the expiry date and/or application period on the pre-printed scale. In order to mark the expiry date and/or any other relevant date, the apparatus 3 comprises a marking, for example an arrow, which is printed on the infusion head 1. This can be achieved using an arrow 7, which is stationary in the apparatus 3 and an infusion head 1 which can be positioned on the apparatus 3 in such a way that the arrow 7 is printed exactly on the desired date, i.e. the infusion head 1 can be placed on the apparatus 3 in any position, like a disc which can be rotated around its central rotational axis.

If a period is to be marked, then two arrows 7 may be utilized in order to mark the beginning of the period and the end of the period. If the period is always of the same length, then two arrows 7 which are fixed in the apparatus can be provided. If, however, the length of the period can vary, the arrows 7 may be movable or at least one arrow 7 may be movable relative to the other arrow 7 in order to adjust the image to be transferred to the length of the actual period. If only one arrow 7 is movable, the infusion head 1 can bear a pre-printed image as described above that is then positioned such that the fixed arrow 7 is transferred onto a desired position (for example the beginning of the application period), while the second arrow 7 can be set to the desired position (for example the end of the application period). If both arrows 7 are movable relative to each other and relative to the apparatus 3, it is preferable for the apparatus 3 to transfer the image representing the time scale and the arrows 7. The infusion head 1 can then be placed on the apparatus 3 in any position.

Figure 4A:
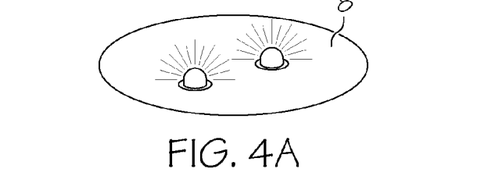
FIG. 4 depicts a display device as an electronic display that includes two illuminants placed on the infusion head, together with the apparatus, in accordance with the various embodiments.
Figure 4B:
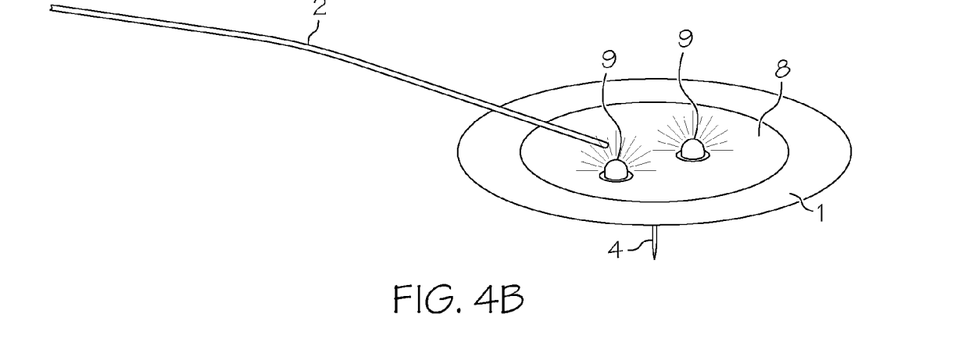

FIG. 4 shows an electronic display 8 that includes at least one illuminant 9 (with two in the example shown) in the form of a light emitting diode (LED) or organic light emitting diode (OLED). The illuminant 9 can be configured to indicate the relevant dates when using an infusion set, such as the expiry date, the beginning and/or end of an application period, the elapsed time of a period, the remaining time of a period and so on. If only one illuminant 9 is provided, the illuminant 9 can, for example, indicate the end of a period by lighting up or by going out or by changing color or by starting to blink at the end of the period. If two or more illuminants 9 are used, the illuminants can indicate the beginning or end of a period as just described above. They can, for example, work in a similar way to traffic lights, where a first color (green) indicates that the period is elapsing, a second color (yellow) indicates that the end of the period is approaching, and a third color (red) indicates the end of the period. Similarly, the illuminants 9 could initially all have the same color and could change color, light up, or go out one after the other, depending on the elapsed time.

Figure 5:
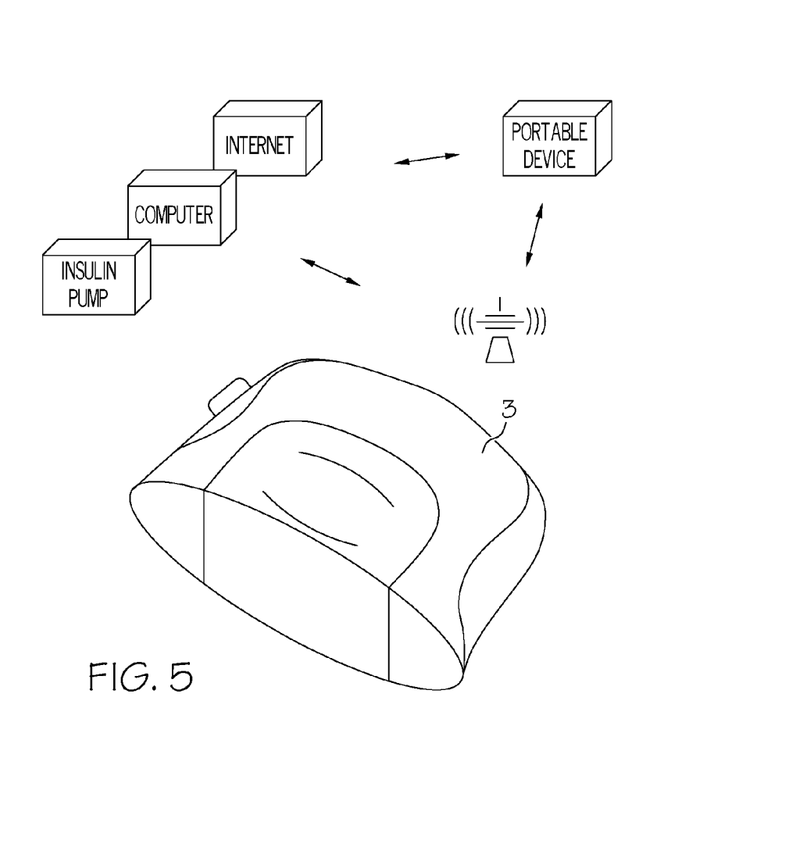
FIG. 5 depicts an apparatus that includes a wireless connection to other electronic devices, in accordance with the various embodiments.

FIG. 5 shows an apparatus 3 that is or can communicate with an electronic device, such as a smart phone, a computer, an insulin pump or the internet. The apparatus 3 preferably communicates with the other device or devices via a BLUETOOTH connection or an infrared remote control connection. In order to ensure that the transferred data are correctly assigned to the patient, the apparatus 3 can include a scanner for scanning in the patient data from a bar code which is, for example, affixed to the patient's sheet. The apparatus 3 can also include an input system, which allows specific dates necessary for uniquely identifying the patient to be entered. Further, a remote control can be provided that enables the staff to input the relevant patient data in the system.

Figure 6:
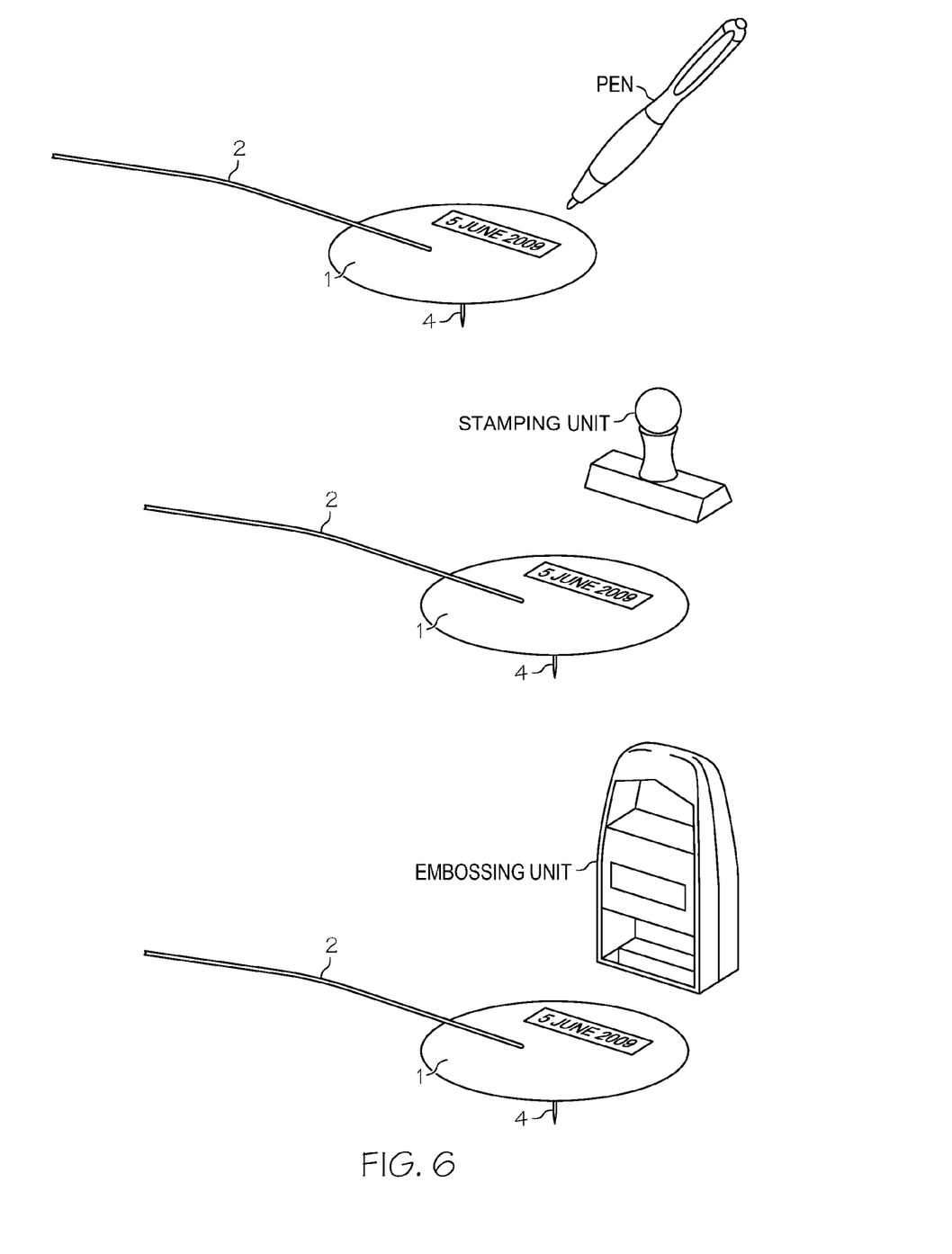
FIG. 6 depicts a display device as a stamp or embossing on an infusion head that includes a special region for stamping, in accordance with the various embodiments.
Figure 7:
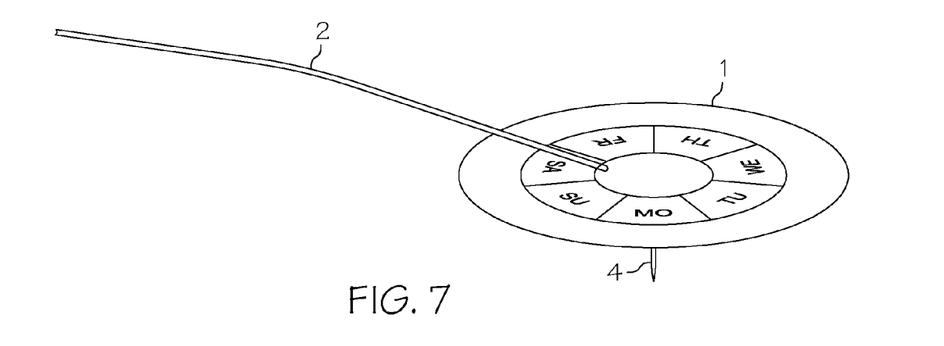
FIG. 7 depicts an infusion head that includes a display device as a sticker, in accordance with the various embodiments.
Figure 8:
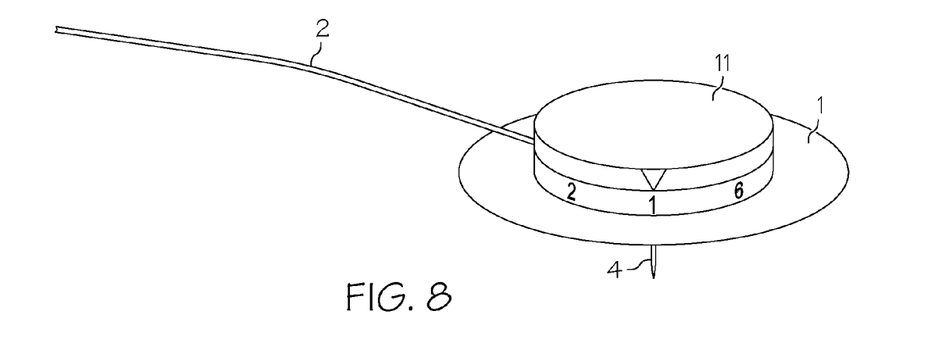
FIG. 8 depicts an infusion head that includes a display device as a mechanical display, in accordance with the various embodiments.

FIGS. 6 to 8 show a device for displaying an expiry date and/or an application period without using the apparatus 3. FIG. 6 shows how the date or period can be stamped or embossed directly onto the surface of the infusion head 1 by an embossing unit, which may be an integrated part of the device. The integrated stamping unit 5 is preferably a stamping unit 5 on which it is possible to set the date which is to appear on the infusion head 1. The date can be set mechanically, or an electronic stamping unit can be used. Instead of stamping or embossing the relevant dates on the infusion head 1, a sticker 10 can be provided that is or can be placed on the infusion head 1 and shows partitions representing hours, days, or other units of time that can easily be marked so as to identify the expiry date and/or the application period. The partitions can be marked with the aid of a pen or by cutting parts off the sticker or by any other suitable manipulation of the sticker. If a certain date is to be displayed, the infusion head 1 can comprise a printed image (such as for example an arrow) that is aligned with the relevant date in order to set the date.

FIG. 7 depicts an infusion head in accordance with the various embodiments, comprising a sticker 10. Also included are the infusion head 1, and the coupler 2.

FIG. 8 shows an infusion head 1 that includes a reusable mechanical display 11. This mechanical display 11 can, for example, include two ring elements or two discs that can be rotated relative to each other, one of which includes a set of numbers and the other, which includes, for example, an arrow in order to mark the beginning of an application. If a period is to be marked, two arrows may be utilized, which can be achieved by using three rings or three discs or by incorporating two separate arrows which can be moved relative to a base plate which displays the countermarks.

Figure 9:
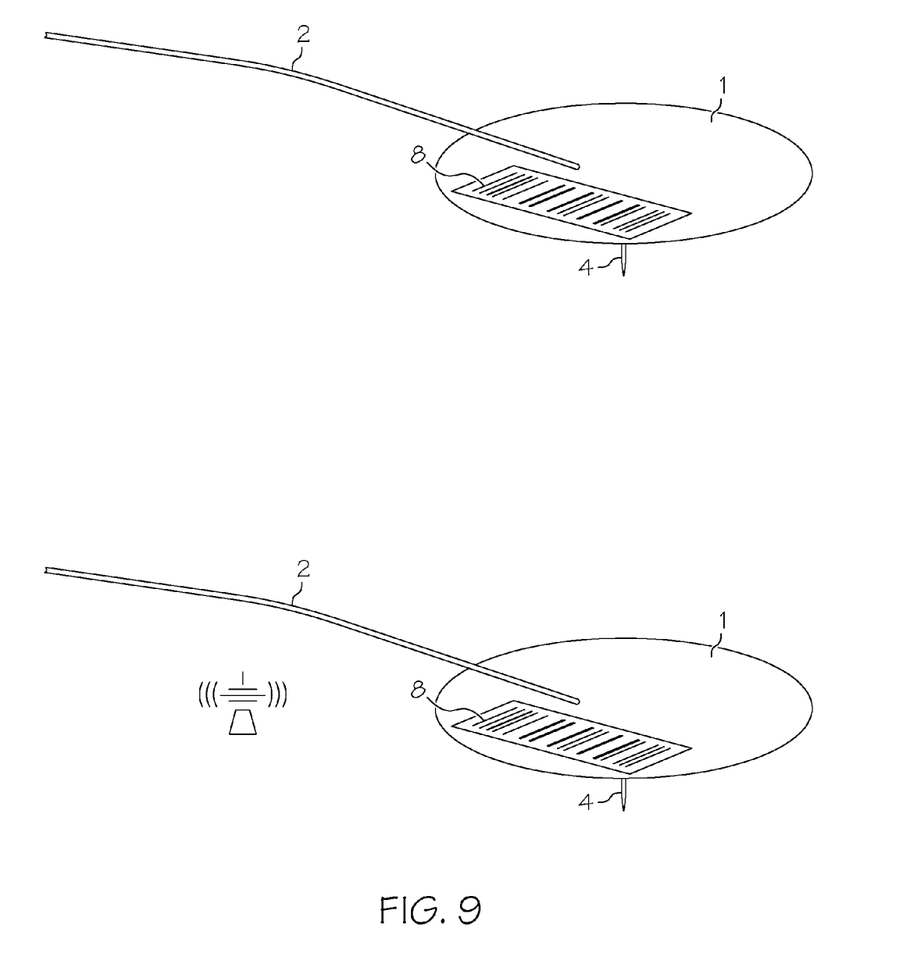
FIG. 9 depicts an infusion head that includes a display device as an electronic display with or without wireless connectivity, in accordance with the various embodiments.

FIG. 9 shows an infusion head 1 comprising an electronic display 8. In some embodiments, all the relevant dates can be displayed. However in some embodiments, the expiry date of the device and/or an application period can be displayed. The digits on the display should be large enough to be easily identifiable with the naked eye. Additional attention can be garnered if the color of the display changes when the end of the period or the expiry date is reached, a blinking display would further increase its conspicuousness. The electronic display 8 may also generate an acoustic signal in order to attract the attention of the staff. The electronic display 8 can further include a connecting device for a wireless connection to different devices, such as, for example, a smart phone, a computer, the internet, or a diabetes management system. A remote control, such as an infrared remote control, can be provided for activating and configuring the electronic display 8.

What has been described above are examples of the subject invention. It is, of course, not possible to describe every conceivable combination of components or methodologies, but one of ordinary skill in the art will recognize that many further combinations and permutations of the subject invention are possible. Accordingly, the subject invention is intended to embrace all such alterations, modifications and variations that fall within the spirit and scope of the claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An infusion set for administering a liquid to a patient, comprising:
    an infusion head placeable on tissue of the patient;
    a coupler that connects the infusion head to an administering device;
    a cannula that connects to the infusion head;
    a display device which displays an application period of at least a portion of the liquid administered using the infusion set; and
    an apparatus for placing the infusion head on the tissue and transferring relevant information onto the display device.

2. The infusion set of claim 1, wherein the display device connects to the infusion head.

3. The infusion set of claim 1, wherein the display device includes a special region for embossing the application period using an embossing unit.

4. The infusion set claim 1, wherein an embossing unit is an integrated part of the apparatus and includes a setting device which sets a beginning of the application period.

5. The infusion set of claim 1, wherein the apparatus includes a wireless connection which connects the apparatus to an electronic device to transfer the beginning of the application period to the electronic device.

6. The infusion set of claim 1, wherein the apparatus further comprises an integrated stamping unit.

7. The infusion set of claim 1, wherein the apparatus further comprises a mechanical date display.

* * * * *

UNITED STATES PATENT AND TRADEMARK OFFICE
CERTIFICATE OF CORRECTION

PATENT NO. : 8,801,671 B2
APPLICATION NO. : 12/878147
DATED : August 12, 2014
INVENTOR(S) : Marcel Mueller et al.

Page 1 of 1

It is certified that error appears in the above-identified patent and that said Letters Patent is hereby corrected as shown below:

In the Specification

Col. 2, Line 2,
"with a including a display device as a date scale printed on it" should read
--with a display device as a date scale printed on it--; and In the Claims Col. 8, Line 20, Claim 4,
"4. The infusion set claim 1, wherein an embossing unit is an" should read
--4. The infusion set of claim 1, wherein an embossing unit is an--.

Signed and Sealed this
Fifth Day of May, 2015

Michelle K. Lee
*Director of the United States Patent and Trademark Office*